United States Patent [19]

Cooper et al.

[11] Patent Number: 5,998,698
[45] Date of Patent: Dec. 7, 1999

[54] TRANSGENIC FISH CAPABLE OF EXPRESSING EXOGENOUS LYTIC PEPTIDES

[75] Inventors: Richard K. Cooper; Frederick M. Enright, both of Baton Rouge, La.

[73] Assignee: Board of Supervisors of Louisiana State University and Agricultural and Mechanical College, Baton Rouge, La.

[21] Appl. No.: 08/491,609

[22] Filed: Jun. 7, 1995

Related U.S. Application Data

[63] Continuation-in-part of application No. PCT/US94/07456, Jun. 30, 1994, which is a continuation-in-part of application No. 08/085,746, Jun. 30, 1993, abandoned, and a continuation-in-part of application No. 08/084,879, Jun. 30, 1993, abandoned.

[51] Int. Cl.$^6$ .................................................. C12N 15/00
[52] U.S. Cl. .............................................................. 800/20
[58] Field of Search ......................... 435/6, 69.1, 172.3, 435/325; 935/6, 9, 34, 55, 70; 800/2, DIG. 1, DIG. 4, 20; 536/23.7, 24.1

[56] References Cited

FOREIGN PATENT DOCUMENTS

| 8900199 | 1/1989 | WIPO | C12N 15/00 |
| 9012866 | 11/1990 | WIPO | C12N 1/06 |
| 9501095 | 1/1995 | WIPO | A01K 67/00 |
| 9501424 | 1/1995 | WIPO | C12N 5/10 |

OTHER PUBLICATIONS

U.S. Ser. No. 373,623, Jaynes et al., filed Jun. 29, 1989.
U.S. Ser. No. 646,449, Jaynes et al., filed Jan. 25, 1991.
U.S. Ser. No. 085,282, Cooper et al., filed Jun. 30, 1993.
Xanthopoulas et al., "The structure of the gene for cecropin B, an antibacterial immune protein from *Hyalophora cecropia*," Eur. J. Biochem., vol. 172, pp. 371–376 (1988).
Kaling et al., "Liver–Specific Gene Expression: A–Activator–Binding Site, a Promoter Module Present in Vitellogen and Acute–Phase Genes," Mol. Cell. Biol., vol. 11, pp. 93–101 (1991).
Boman et al., "Cell–free immunity in Cecropia," Eur. J. Biochem., vol. 201, pp. 23–31 (1991).
Beck et al., "Invertebrate Cytokines III: Invertebrate Interleukin–1–like Molecules Stimulate Phagocytosis by Tunicate and Echinoderm Cells," Cellular Immunology, vol. 146, pp. 284–299 (1993).
Caput et al., "Identification of a common nucleotide sequence in the 3'–untranslated region of mRNA molecules specifying inflammatory mediators," Proc. Natl. Acad. Sci. USA, vol. 83, pp. 1670–1674 (1986).
Morvan et al., "In vitro activity of the antimicrobial peptide magainin 1 against *Bonamia ostreae*, the intrahemocytic parasite of the flat oyster *Ostrea edulis*," Mol. Mar. Biol., vol. 3, pp. 327–333 (1994).
Cooper et al., "Transgenic Catfish Expressing a Lytic Peptide Gene," in Research and Review, A Compilation of Abstracts of Research on Channel Catfish, Catfish Farmers of America (1995).

A. Miller, "Human Gene Therapy Comes of Age," Nature, vol. 357, pp. 455–460 (1992).
P. Klysten et al., "The cecropin locus in Drosophila; a Compact Gene Cluster Involved in the Response to Infection," E.M.B.O. J., vol. 9, pp. 217–224 (1990).
J. Reichhart et al., "Insect Immunity: Developmental and Inducible Activity of the Drosophila Diptericin Promoter," E.M.B.O. J. vol. 11, pp. 1469–1477 (1992).
Y. Tryselius et al., "CecC, a Cercropin Gene Expressed During Metamorphosis in Drosophila Pupae," Eur. J. Biochem., vol. 204, pp. 395–399 (1992).
G. Ciliberto et al., "Inducible and Tissue–Specific Expression of Human C–reactive Protein in Transgenic Mice," E.M.B.O. J., vol. 6, pp. 4017–4022 (1987).
Pelham et al., "DNA Sequences Required for Transcriptional Regulation of the *Drosophila* hsp70 Heat–Shock Gene in Monkey Cells and *Xenopus* Oocytes," in (Schlessinger et al., eds.) *Heat Shock From Bacteria ato Man*, Cold Spring Harbor Laboratory, Cold Spring Harbor, NY, pp. 43–48 (1982).
U.S. application No. 07/069,653, Jaynes et al., filed Jul. 6, 1987.
U.S. application No. 07/102,175, Jaynes et al., filed Sep. 29, 1987.
U.S. application No. 07/336,181, Jaynes et al., filed Apr. 10, 1989.
E. Cameron et al. Br. Vet. J. 150: 9–24 (1994).
R. Guyonard et al. Biochemie 71: 857–63 (1989).
T. Chen. Trnasgenic Models in Med & Agric. Wiley–Liss (1990) pp. 127–139.

*Primary Examiner*—Bruce R. Campbell
*Attorney, Agent, or Firm*—John H. Runnels

[57] ABSTRACT

Novel means have been discovered for increasing the resistance of an animal host (including humans) to diseases caused by intracellular bacteria, protozoa, and viruses. The infection treated may, for example, be equine infectious anemia, or infection by the human immunodeficiency virus. Novel means have also been found for treating tumors Augmentation of the host's defenses against infectious diseases or tumors is achieved by "arming" the host's cells with an exogenous gene encoding a natural or synthetic lytic peptide. For example, the transfection of hematopoietic stem cells and embryonic cells will produce animals with enhanced disease resistance; and transfection of TIL (tumor infiltrating lymphocytes) cells or other cells can be used in the treatment of tumors. Genes coding for a cecropin or other native or synthetic lytic peptide can be transferred and stably expressed in mammalian, bony fish, other vertebrate, and other animal cells. The transformed cells have the ability to produce and secrete a broad spectrum chemotherapeutic agent that has a systemic effect on certain pathogens, particularly pathogens that might otherwise evade or overcome host defenses.

3 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

AGACTTGACT CCGCTGCATA AGTG                          24

(2) INFORMATION FOR SEQ ID NO:2:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

TACCGTTTCT GATGTTGCGA CC                                                      22

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

TTTTCTTCGT GTTCGCTTTG GTTCTG                                                  26

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

ATCGCCGGTC CAGCCTTGAC AATAC                                                   25
```

TRANSGENIC FISH CAPABLE OF EXPRESSING EXOGENOUS LYTIC PEPTIDES

This is a continuation-in-part of International Application No. PCT/US94/07456, international filing date Jun. 30, 1994; which in turn is a continuation-in-part of two prior United States patent applications. (1) U.S. patent application Ser. No. 08/085,746, filed Jun. 30, 1993, now abandoned; and (2) U.S. patent application Ser. No. 08/084,879, filed Jun. 30, 1993, now abandoned.

The development of this invention was partially funded by the Government under grants 90364-5137 and 903-64-3105 awarded by the Department of Agriculture. The Government may have certain rights in this invention.

This invention pertains to transgenic fish and transgenic fish cells capable of expressing exogenous lytic peptides.

Lytic Peptides

Few effective treatments exist for either acute or chronic intracellular bacterial, protozoal, or viral diseases of animals, including humans. In many such infections, the infectious agent is localized within host cells. Due to the intracellular location of the infectious agents, the host immune system is often ineffective. Likewise, antipathogenic compounds are often ineffective, due to their difficulty in crossing host cell membranes.

Beck et al., "Invertebrate Cytokines III: Invertebrate Interleukin-1-like Molecules Stimulate Phagocytosis by Tunicate and Echinoderm Cells," Cellular Immunology, vol. 146, pp. 284–299 (1993) discusses relationships among phagocytotic mechanisms of different phyla.

Lytic peptides are small, basic proteins. Native lytic peptides appear to be major components of the antimicrobial defense systems of a number of animal species, including those of insects, amphibians, and mammals. They typically comprise 23–39 amino acids, and have the potential for forming amphipathic alpha-helices. See Boman et al., "Humoral immunity in Cecropia pupae," Curr. Top. Microbiol. Immunol. vol. 94/95, pp. 75–91 (1981); Boman et al., "Cell-free immunity in insects," Annu. Rev. Microbiol., vol. 41, pp. 103–126 (1987); Zasloff, "Magainins, a class of antimicrobial peptides from Xenopus skin: isolation, characterization of two active forms, and partial DNA sequence of a precursor," Proc. Natl. Acad. Sci. USA, vol. 84, pp. 3628–3632 (1987); Ganz et al., "Defensins natural peptide antibiotics of human neutrophils," J. Clin. Invest., vol. 76, pp. 1427–1435 (1985); and Lee et al., "Antibacterial peptides from pig intestine: isolation of a mammalian cecropin," Proc. Natl. Acad. Sci. USA, vol. 86, pp. 9159–9162 (1989).

Known amino acid sequences for lytic peptides may be modified to create new peptides that would also be expected to have lytic activity by substitutions of amino acid residues that preserve the amphipathic nature of the peptides (e.g., replacing a polar residue with another polar residue, or a non-polar residue with another non-polar residue, etc.); by substitutions that preserve the charge distribution (e.g., replacing an acidic residue with another acidic residue, or a basic residue with another basic residue, etc.); or by lengthening or shortening the amino acid sequence while preserving its amphipathic character or its charge distribution. Lytic peptides and their sequences are disclosed in Yamada et al., "Production of recombinant sarcotoxin IA in Bombyx mori cells," Biochem. J., Vol. 272, pp. 633–666 (1990); Taniai et al., "Isolation and nucleotide sequence of cecropin B cDNA clones from the silkworm, Bombyx mori." Biochimica Et Biophysica Acta, Vol. 1132, pp. 203–206 (1992); Boman et al., "Antibacterial and antimalarial properties of peptides that are cecropin-melittin hybrids," Febs Letters, Vol. 259, pp. 103–106 (1989); Tessier et al., "Enhanced secretion from insect cells of a foreign protein fused to the honeybee melittin signal peptide," Gene, Vol. 98, pp. 177–183 (1991); Blondelle et al., "Hemolytic and antimicrobial activities of the twenty-four individual omission analogs of melittin," Biochemistry, Vol. 30, pp. 4671–4678 (1991); Andreu et al., "Shortened cecropin A-melittin hybrids. Significant size reduction retains potent antibiotic activity," Febs Letters, Vol. 296, pp. 190–194 (1992); Macias et al., "Bactericidal activity of magainin 2: use of lipopolysaccharide mutants," Can. J. Microbiol., Vol. 36, pp. 582–584 (1990); Rana et al., "Interactions between magainin-2 and Salmonella typhimurium outer membranes: effect of Lipopolysaccharide structure," Biochemistry, Vol. 30, pp. 5858–5866 (1991); Diamond et al., "Airway epithelial cells are the site of expression of a mammalian antimicrobial peptide gene," Proc. Natl. Acad. Sci. USA, Vol. 90, pp. 4596ff(1993); Selsted et al., "Purification, primary structures and antibacterial activities of β-defensins, a new family of antimicrobial peptides from bovine neutrophils," J. Biol. Chem., Vol. 268, pp. 6641 ff(1993); Tang et al., "Characterization of the disulfide motif in BNBD-12, an antimicrobial β-defensin peptide from bovine neutrophils," J. Biol. Chem., Vol. 268, pp. 6649 ff (1993); Lehrer et al., Blood, Vol. 76, pp. 2169–2181 (1990); Ganz et al., Sem. Resp. Infect. I., pp. 107–117 (1986); Kagan et al., Proc. Natl. Acad. Sci. USA, Vol. 87, pp. 210–214 (1990); Wade et al., Proc. Natl. Acad. Sci. USA, Vol. 87, pp. 4761–4765 (1990); and Romeo et al., J. Biol. Chem., Vol. 263, pp. 9573–9575 (1988).

Lytic peptides typically have a broad spectrum of activity (e.g., against gram negative bacteria, fungi, protozoa, and viruses). Their activity is both direct and indirect (e.g., virus-infected cells are destroyed, disrupting virus production) Thus some pathogens that have developed the ability to avoid host defenses are nevertheless susceptible to destruction by lytic peptides.

At least four families of naturally-occurring lytic peptides have been discovered in the last decade: cecropins, defensins, sarcotoxins, and magainins. Boman and coworkers in Sweden performed the original work on the humoral defense system of *Hyalophora cecropia*, the giant silk moth, to protect itself from bacterial infection. See Hultmark et al., "Insect immunity. Purification of three inducible bactericidal proteins from hemolymph of immunized pupae of *Hyalophora cecropia*," Eur. J. Biochem., vol. 106, pp. 7–16 (1980); and Hultmark et al., "Insect immunity. Isolation and structure of cecropin D. and four minor antibacterial components from cecropia pupae," Eur. J. Biochem., vol. 127, pp. 207–217 (1982).

Infection in *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence that will form an amphipathic alpha-helix. Andrequ et al., "N-terminal analogues of cecropin A: synthesis, antibacterial activity, and conformational properties," Biochem., vol. 24, pp. 1683–1688 (1985). The carboxy-terminal half of the peptide comprises a hydrophobic tail. See also Boman et al., "Cell-free immunity in Cecropia," Eur. J. Biochem., vol. 201, pp. 23–31 (1991).

Recently, a cecropin-like peptide has been isolated from porcine intestine. Lee et al., "Antibacterial peptides from pig intestine: isolation of a mammalian cecropin," Proc. Natl. Acad. Sci. USA, vol. 86, pp. 9159–9162 (1989).

Cecropin peptides have been observed to kill a number of animal pathogens other than bacteria. See Jaynes et al., "In Vitro Cytocidal Effect of Novel Lytic Peptides on *Plasmodium falciparum* and *Trypanosoma cruzi*," FASEB, 2878–2883 (1988); Arrowood et al., "Hemolytic properties of lytic peptides active against the sporozoites of *Cryptosporidium parvum*," J. Protozool., vol. 38, No. 6, pp. 161S–163S (1991); and Arrowood et al., "In vitro activities of lytic peptides against the sporozoites of *Cryptosporidium parvum*," Antimicrob. Agents Chemother., vol. 35, pp. 224–227 (1991). However, normal mammalian cells do not appear to be adversely affected by cecropins, even at high concentrations. See Jaynes et al., "In vitro effect of lytic peptides on normal and transformed mammalian cell lines," Peptide Research, vol. 2, No. 2, pp. 1–5 (1989); and Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992).

Defensins, originally found in mammals, are small peptides containing six to eight cysteine residues. Ganz et al., "Defensins natural peptide antibiotics of human neutrophils," J. Clin. Invest., vol. 76, pp. 1427–1435 (1985). Extracts from normal human neutrophils contain three defensin peptides: human neutrophil peptides HNP-1, HNP-2, and HNP-3. Defensin peptides have also been described in insects and higher plants. Dimarcq et al., "Insect immunity: expression of the two major inducible antibacterial peptides, defensin and diptericin, in *Phormia terranvae*," EMBO J., vol. 9, pp. 2507–2515 (1990); Fisher et al., Proc. Natl. Acad. Sci. USA, vol. 84, pp. 3628–3632 (1987).

Slightly larger peptides called sarcotoxins have been purified from the fleshfly *Sarcophaga peregrina*. Okada et al., "Primary structure of sarcotoxin I, an antibacterial protein induced in the hemolymph of *Sarcophaga peregrina* (flesh fly) larvae," J. Biol. Chem., vol. 260, pp. 7174–7177 (1985). Although highly divergent from the cecropins and defensins, the sarcotoxins presumably have a similar antibiotic function.

Other lytic peptides have recently been found in amphibians. Gibson and collaborators isolated two peptides from the African clawed frog, *Xenopus laevis*, peptides which they named PGS and Gly$^{10}$Lys$^{22}$PGS. Gibson et al., "Novel peptide fragments originating from PGL$_a$ and the caervlein and xenopsin precursors from *Xenopus laevis*," J. Biol. Chem., vol. 261, pp. 5341–5349 (1986); and Givannini et al., "Biosynthesis and degradation of peptides derived from *Xenopus laevis* prohormones," Biochem. J., vol. 243, pp. 113–120 (1987). Zasloff showed that the Xenopus-derived peptides have antimicrobial activity, and renamed them magainins. Zasloff, "Magainins, a class of antimicrobial peptides from Xenopus skin: isolation, characterization of two active forms, and partial DNA sequence of a precursor," Proc. Natl. Acad. Sci. USA, vol. 84, pp. 3628–3632 (1987).

Synthesis of nonhomologous analogs of different classes of lytic peptides has been reported to reveal that a positively charged, amphipathic sequence containing at least 20 amino acids appeared to be a requirement for lytic activity. Shiba et al., "Structure-activity relationship of Lepidopteran, a self-defense peptide of Bombyx more," Tetrahedron, vol. 44, No. 3, pp.787–803 (1988); and unpublished data from our laboratory. The published literature has reported that a 20-mer appeared to possess roughly the minimum alpha-helix length needed to span a cell membrane. Smaller peptides (or lower concentrations of peptide) not only failed to kill cells, but were reported actually to stimulate cell growth. Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992).

Cecropins have been shown to target pathogens or compromised cells selectively, without affecting normal host cells. The synthetic lytic peptide known as Shiva 1 has been shown to destroy intracellular *Brucella abortus*-, *Trypanosoma cruzi*-, *Cryptosporidium parvum*-, and infectious bovine herpes virus I (IBR)-infected host cells, with little or no toxic effects on noninfected mammalian cells. See Jaynes et al., "In vitro effect of lytic peptides on normal and transformed mammalian cell lines," Peptide Research, vol. 2, No. 2, pp. 1–5 (1989); Wood et al., "Toxicity of a Novel Antimicrobial Agent to Cattle and Hamster cells In vitro," Proc. Ann. Amer. Soc. Anim. Sci., Utah State University, Logan, UT. J. Anim. Sci. (Suppl. 1), vol. 65, p. 380 (1987); Arrowood et al., "Hemolytic properties of lytic peptides active against the sporozoites of *Cryptosporidium parvum*," J. Protozool., vol. 38, No. 6, pp. 161S–163S (1991); Arrowood et al., "In vitro activities of lytic peptides against the sporozoites of *Cryptosporidium parvum*," Antimicrob. Agents Chemother., vol. 35, pp. 224–227 (1991); and Reed et al., "Enhanced in vitro growth of murine fibroblast cells and preimplantation embryos cultured in medium supplemented with an amphipathic peptide," Mol. Reprod. Devel., vol. 31, No. 2, pp. 106–113 (1992).

Morvan et al., "In vitro activity of the antimicrobial peptide magainin 1 against *Bonamia ostreae*, the intrahemocytic parasite of the flat oyster *Ostrea edulis*," Mol. Mar. Biol., vol. 3, pp. 327–333 (1994) reports the in vitro use of a magainin to selectively reduce the viability of the parasite *Bonamia ostreae* at doses that did not affect cells of the flat oyster *Ostrea edulis*.

Also of interest are the following commonly-assigned patent applications: Jaynes et al., "Method for Introduction of Disease and Pest Resistance Into Plants and Novel Genes Incorporated Into Plants Which Code Therefor," United States patent application Ser. No. 07/373,623, filed Jun. 29, 1989 abandoned; Jaynes et al., "Plants Genetically Enhanced for Disease Resistance," United States patent application Ser. No. 07/646,449, filed Jan. 25, 1991 abandoned; Jaynes et al., "Therapeutic Antimicrobial Polypeptides, Their Use and Methods for Preparation," Ser. No. 07/069,653, filed Jul. 6, 1987 abandoned; Jaynes et al., "Inhibition of Eucaryotic Pathogens and Neoplasms and Stimulation of Fibroblasts and Lymphocytes with Lytic Peptides," United States patent application Ser. No. 07/102, 175, filed Sep. 29, 1987 abandoned; Jaynes, "Lytic Peptides: Their Use in the Treatment of Microbial Infections, Cancer and in the Promotion of Growth," United States patent application Ser. No. 07/336,181, filed Apr. 10, 1989 abandoned; and McLaughlin et al., "Amphipathic Peptides," United States patent application Ser. No. 08/232,525, filed Apr. 22, 1994 abandoned.

It is believed (without wishing to be bound by this theory) that lytic peptides act by disrupting cell membranes, and that normal host cells protect themselves through their ability to repair the resulting membrane damage. By contrast, bacteria, protozoa, and compromised host cells are unable (or less able) to repair damaged membranes. Because parasitized cells have a diminished capacity to repair membranes, after a lytic peptide "attack" they are preferentially destroyed, while adjacent normal cells repair their membranes and survive.

At least three modes have been proposed for the lytic peptide-membrane interaction that leads to cytolysis: (1)

The amphipathic helix is located on the membrane surface, and the presence of the helix in the head group region disorders the lipid bilayer. Dawson et al., "The interaction of bee melittin with lipid bilayer membranes," Biochem. Biophys. Acta., vol. 510, pp. 75–86 (1978). (2) Peptide oligomers form ion channels in the membrane, resulting in osmotically-induced lysis. Tosteson et al., "The sting—melittin forms channels in lipid bilayers," Biophys. J., vol. 36, pp. 109–116 (1981). (3) The lytic peptide causes aggregation of native membrane proteins, resulting in the formation of channels or pores. Burt et al., "Role of membrane proteins in monosodium urate crystal-membrane interactions. I. Effect of pretreatment of erythrocyte neuraminidase," J. Rheumatol., vol. 17, pp. 1353–1358 (1990).

Many intracellular obligate pathogens live inside host cells because they are vulnerable to host defenses when outside the cell, where they may be destroyed by humoral or cellular defenses, or by conventional therapeutic agents. Also, known viruses and intracellular protozoa require a staging development within a host cell before becoming infectious; if released prematurely they will not be infective. Evidence indicates that the released infective stages in bacterial, fungal, and protozoal pathogens are directly destroyed by lytic peptides. See Jaynes et al., "In vitro effect of lytic peptides on normal and transformed mammalian cell lines," Peptide Research, vol. 2, No. 2, pp. 1–5 (1989); Jaynes et al., "In Vitro Cytocidal Effect of Novel Lytic Peptides on *Plasmodium falciparum* and *Trypanosoma cruzi*," FASEB, 2878–2883 (1988); Arrowood et al., "Hemolytic properties of lytic peptides active against the sporozoites of *Cryptosporidium parvum*," J. Protozool., vol. 38, No. 6, pp. 161S–163S (1991); and Arrowood et al., "In vitro activities of lytic peptides against the sporozoites of *Cryptosporidium parvum*," Antimicrob. Agents Chemother., vol. 35, pp. 224–227 (1991).

Plants Transformed with Lytic Peptide Genes

A number of synthetic lytic peptides have been synthesized, retaining some properties of native lytic peptides. For example, Shiva I was designed as a substitution analog of native Cecropin B, having 46% homology to the natural Cecropin B molecule. However, the hydrophobic properties and charge density of the native structure were conserved in the synthetic peptide. Data supporting the ability of the Shiva I gene to enhance disease resistance has been obtained from transgenic plants. Genes encoding synthetic lytic peptides were chemically synthesized and cloned into the binary vector pBI121. For the less active peptide SB-37 (a cecropin analog), expression was controlled by a constitutive promoter, the 35S cauliflower mosaic virus 5' region-nopaline synthetase-3' polyadenylation cassette (Rogers et al. "Improved vectors for plant transformation expression cassette vectors and new selectable markers," Meth. Enz. vol. 153, pp. 253–305 (1987)). For the more active Shiva I, expression was controlled by the wound-inducible plant promoter for proteinase inhibitor II ("PiII") (Sanchez-Serrano et al., "Wound-induced expression of a potato proteinase inhibitor II gene in transgenic tobacco plants," EMBO J. vol. 6, pp. 303–306 (1987); Jaynes et al., "Expression of a cecropin B lytic peptide analog in transgenic tobacco confers enhanced resistance to bacterial wilt caused by *Pseudomonas solanacearum*," Plant Science (1993).

In non-wounded potato plants, PiII accumulates in the tubers, with non-detectable levels of the protein in leaves, stem or roots. When the leaves are wounded, however, expression of the gene is induced not only in the wounded leaves, but also in non-wounded upper and lower leaves and in the upper part of the stem. Pena-Cortes et al., "Systemic induction of proteinase-inhibitor-II gene expression into potato plants by wounding," Planta, vol. 174, pp. 84–91 (1988).

Transgenic tobacco plants with genes coding for lytic peptides have also been obtained via Agrobacterium transformation. Bioassays testing the disease resistance of $F_1$ progeny indicated that, compared to transgenic controls and SB-37 plants, Shiva-containing tobacco seedlings exhibited delayed wilt symptoms and reduced disease severity and mortality after infection with a highly virulent strain of *Pseudomonas solanacearum*. (*P. solanacearum* is a vascular pathogen that causes severe wilting.) Jaynes et al., "Expression of a cecropin B lytic peptide analog in transgenic tobacco confers enhanced resistance to bacterial wilt caused by *Pseudomonas solanacearum*," Plant Science (1993). No enhanced resistance was observed for the plants producing the synthetic peptide SB-37, presumably because of its low bioactivity against this pathogen. Destefano-Beltran et al., Mol. Biol. of the Potato, pp. 205–221 (1990).

In contrast to this work in plants, to the knowledge of the inventors, no previous work has resulted in the successful expression of exogenous cecropin (or any other lytic peptide) in mammalian or other animal cells. In fact, very few invertebrate genes have ever been stably expressed in a vertebrate cell, and even fewer non-mammalian genes have ever been stably expressed in a mammalian cell.

Transformation of Eukaryotic Genomes

A major problem in transforming DNA into eukaryotic cells, especially into the cells of mammals and other vertebrates, is the stable integration of the exogenous DNA into a recipient chromosome. Several techniques are currently used for the delivery of the DNA into the recipient host, techniques that have shown varying degrees of success. The first, and currently most common, method for transformation of animals is the microinjection of exogenous DNA into a one- or two-cell embryo. This procedure has several drawbacks, including the following difficulties: (1) the technique requires a level of skill that is not available in most laboratories; (2) the procedure is very time-consuming, often requiring an entire day to microinject a few hundred embryos; and (3) the method has a relatively low success rate—typically about 1–3% of the injected embryos are observed to have a stable insertion.

The second most common procedure is electroporation. Electroporation has advantages over microinjection, primarily in speed. Using electroporation, several thousand embryos can be transformed in a day. Major limitations include the following: (1) the availability of embryos, (2) means to maintain and screen the embryos and (3) the approximately 50% lethality levels caused by the electric currents typically used. The high lethality is somewhat offset by the increased number of embryos demonstrating positive expression, a number that can approach 15%, about five times that of the best microinjection rates.

A third method, currently gaining popularity, is the use of lipofection to deliver DNA packaged inside liposomes. Lipofection has the advantage over electroporation that it is not as lethal to the cells. Lipofection typically results in a 1–2% increase in successful transformations as compared to electroporation.

However, each of these three transformation methods shares the common disadvantage of relying on homologous recombination of the target DNA into recipient chromosomal DNA; the necessary homologies may not always exist, and even where they do exist, the recombination events may be slow. In addition, each of the above percentages for successful DNA expression is decreased by a factor of approximately two if the only insertions counted are those that are successfully passed on to subsequent generations of cells or offspring.

Because the limiting factor for most transformations is typically the availability of embryos, it is desirable to optimize the chances of stable DNA insertion into the available embryos. An embryo, regardless of source, should be in the 2–4 cell stage of development to maximize the probability of a stable insertion that will be incorporated into the germ cells. Obtaining embryos at this stage requires careful timing; and a quick response time will often be necessary to ensure that the cells are manipulated while in the proper stage, before their development progresses too far.

Current procedures for the genetic transformation of higher organisms are not only time-consuming, but are also expensive in terms of person-hours used. For these and other reasons, there remains an unfilled need for a more efficient means of delivering and stably integrating exogenous DNA into the chromosomes of a higher organism.

Transposons

A transposon is a mobile genetic element capable of inserting at random into a DNA sequence. See generally Lewin, Genes IV, pp. 649–671 (1990); and Lewin, Genes V, pp. 999–1031 (1994). Most prior research on transposons has been conducted with bacteria; a limited number of studies have been conducted with transposons in eukaryotic cells. A wild-type transposon typically includes a gene encoding a transposase (an enzyme controlling transposition), flanked by two sequences called insertion sequences. It may also carry other genes, such as a gene for antibiotic resistance. The insertion sequences are generally inverted repeats of one another (exact or closely related). Wild-type transposons typically insert preferentially in certain regions or "hot spots" in the host genome.

Prior work with transposons has used transposons for creating mutations, e.g., disrupting existing genes; and in studying pathogenesis. In such applications, unmodified wild-type transposons have several disadvantages. These disadvantages include undesired homologous recombinations resulting from the relatively large size of the insertion sequences, and spontaneous transposition of a transposon to another location in the genome induced by the transposase. Spontaneous transposition is relatively rare, but it can cause the expression of a new phenotypic trait, making interpretation of results difficult.

"Mini-transposons" have recently been developed to attempt to circumvent some of the problems associated with wild-type transposons. Kleckner et al., "Uses of Transposons with Emphasis on Tn10," pp. 139–180 in Miller (ed.), *Methods in Enzymology*, vol. 204 (1991). These mini-transposons have been modified from the wild-type transposons in three ways: (1) The transposase gene has been removed from its native site between the two insertion sequences, and instead placed upstream from the transposon. This rearrangement promotes a more stable insertion that should not move following insertion, because the transposase gene is lost upon insertion. (2) The insertion sequences have been shortened to about 70 base pairs in length, compared to sequences that are typically well over 100 base pairs in wild-type transposons. This shorter length greatly inhibits unwanted homologous recombinations. (3) The entire transposon "cassette" has been placed under the control of an inducible promoter, such as the ptac promoter. The ptac promoter is only read in the presence of isopropyl-β-D-thiogalactopyranoside (IPTG), allowing complete control over when the transposase is activated to cause transposition of the transposon. Furthermore, the transposase is often mutated so that it is less specific to "hot spots," sequences where the wild-type transposon preferentially inserts. This lowered specificity increases the rate of insertion into the genome.

Mini-transposons have previously been used in place of wild-type transposons to cause mutations by disrupting genes, and to study pathogenesis. It has not previously been suggested that a mini-transposon might be used as a vector for stably transforming an exogenous gene into a eukaryotic chromosome.

THE INVENTION

Novel means have been discovered for increasing the resistance of a mammalian (including human), vertebrate, or invertebrate host to diseases caused by intracellular bacteria, protozoa, and viruses The infection treated may, for example, be equine infectious anemia, or infection by the human immunodeficiency virus. Novel means have also been found for treating tumors.

Augmentation of the host's defenses against infectious diseases or tumors is achieved by "arming" the host's cells with an exogenous gene. The host's own leukocytes, other cells involved in resistance to infection, or other cells are transformed with a gene conferring the ability to synthesize and secrete natural or synthetic lytic peptides, such as native cecropin B or synthetic lytic peptides such as SB-37, Shiva I through X, or Manitou. The expression of the genes is induced when needed to combat pathogens.

For example, the transfection of hematopoietic stem cells and embryonic cells will produce animals (or humans) with enhanced disease resistance; and transfection of leukocytes such as TIL (tumor infiltrating lymphocytes) cells, neutrophils, macrophages, or cytotoxic lymphocytes can be used in the treatment of tumors. Stable incorporation of the gene into an egg, a zygote, an early-stage embryo, or a totipotent embryonal stem cell will cause the gene to be carried in germ cells, and thus to be inherited by future generations. Such a transformed animal (e.g., a chicken or a catfish) would have economic significance.

Transgenic animals that have been or that will be engineered with genes and promoters in accordance with the present invention include domesticated donkeys, horses, cows, sheep, goats, pigs, chickens, and turkeys; as well as various species that are raised or that may be raised in whole or in part through aquaculture, including bony fish, crustaceans, and bivalves such as the following: channel catfish, koi, red drum, hybrid striped bass, trout sp., salmon sp., shrimp sp., lobster sp., crawfish spa, crab sp., and oyster sp.

It has been discovered that genes coding for a cecropin or other native or synthetic lytic peptide, such as native cecropin B or Shiva 1, can be transferred and stably expressed in mammalian, other vertebrate, and other animal cells. The transformed cells have the ability to produce and secrete a broad spectrum chemotherapeutic agent that has a systemic effect on certain pathogens, particularly pathogens that might otherwise evade or overcome host defenses. The peptide's expression is preferably induced only in areas of infection, where it will most effectively augment the host's defense systems. Animal cells, including mammalian cells and fish cells, have been transfected with cecropin B, and will also be transfected with cecropin analogs. It has been observed that expression of the exogenous gene does not damage a healthy recipient cell.

Novel means have also been discovered for transforming a eukaryotic cell with a gene under the control of an exogenous promoter that is responsive to an inducer of an acute-phase peptide or protein. As an example, it was unexpected that the transfer of a gene coding for an invertebrate lytic peptide, or a synthetic homolog of such a peptide, can enhance the immune potential of a vertebrate animal. It is particularly unexpected that placing (or leaving) the gene under the control of a native invertebrate promoter such as the native *Hyalophora cecropia* promoter leads to appropriately induced expression in vertebrate cells. To our knowledge, the stable insertion and expression of a gene in a vertebrate cell under the control of an invertebrate promoter have never previously been accomplished. To our knowledge, the stable insertion and expression of a gene in a eukaryotic cell under the control of an exogenous promoter responsive to an inducer of an acute phase protein has never previously been accomplished.

A novel transposon-based vector has also been developed, a novel vector that enhances the integration of DNA into a host genome, particularly a eukaryotic genome. The novel vector has been used, for example, in the transformation of mammalian and fish cells with a gene coding for the lytic peptide cecropin B. The novel vector allows the rapid and efficient transformation of a eukaryotic genome. Its use does not require the high level of skill needed for microinjections. Nor does it rely on homologous recombination events for a successful transformation, as do the prior methods of microinjection, electroporation, and lipofection.

These and other advantages were achieved by constructing a novel modification of mini-transposons to adapt them to carry a gene of interest into a genome. Such an adaptation of mini-transposons has never previously been suggested.

Briefly, the novel vector for transforming an exogenous gene into a eukaryotic cell comprises: a gene encoding a transposase; two transposon insertion sequences; an exogenous gene, where the exogenous gene is located between the two insertion sequences; and a promoter that is adapted to cause the transcription of the transposase, where one of the insertion sequences is located between the transposase gene and the exogenous gene; and where the transposase is adapted to excise from the vector a fragment comprising the two insertion sequences and the portion of the vector between the two insertion sequences, and to insert the excised fragment into a chromosome of a eukaryotic cell.

This arrangement insures that the transposase gene is not incorporated into the target chromosome, insuring that the transformation will be stable. Descendants of a cell transformed with the vector will not have a copy of the transposase gene. Without a transposase gene to encode a transposase, there will be nothing to promote excision of the exogenous gene from the genome.

The examples given below use a vector based on the Tn10 transposon, but analogous vectors constructed from other transposons will work in the present invention as well. Examples of transposons are known in the art, and include, for example, AC7, Tn5SEQ1, Tn916, Tn951, Tn1721, Tn2410, Tn1681, Tn1, Tn2, Tn3, Tn4, Tn5, Tn6, Tn9, Tn30, Tn101, Tn903, Tn501, Tn1000(γδ), Tn1681, Tn2901, AC transposons, Mp transposons, Spm transposons, En transposons, Dotted transposons, Mu transposons, Ds transposons, dSpm transposons, and I transposons.

All transposons function in an essentially similar manner, so the transposon used to construct novel vectors in accordance with this invention is a matter of choice. The insertion sequences of a transposon will recognize their target sequences (typically 8–10 base paris in length), regardless of the species in whose genome the target sequences are found; and they will insert into the target sequence the DNA lying between the flanking insertion sequences. Target sequences for a given transposon will occur in a genome at a statistically predictable frequency, such that it is statistically likely that any given eukaryotic genome will have multiple target sequences for the insertion sequences from any given transposon.

General

Studies in our laboratory have shown that a variety of treatments make cells susceptible to at least some lytic peptides, in situations where corresponding untreated cells are resistant to the peptides. Resistant cells can be made susceptible by treatment with cytoskeletal inhibitors, cytochalasin D and colchicine, or by chilling the cells to 4° C. for 15 minutes prior to exposure to peptide. Resistant cells treated with trypsin also became extremely susceptible to lysis by the lytic peptides. A common factor in each of these examples of induced susceptibility appears to be an altered plasma membrane and/or cytoskeleton. The alteration may interfere with the repair of damaged membrane by hampering endocytosis or exocytosis.

Further evidence of the selective susceptibility of macrophages to the lytic peptides was obtained in a series of experiments using mouse peritoneal macrophages and *Listeria monocytogenes,* an obligate intracellular, gram-positive bacterium. Normal, non-activated, resident peritoneal macrophages (R1); and activated macrophages derived from the peritoneal cavities of Listeria-immune mice inoculated intra-peritoneally 17 hours earlier with Listeria (L1) were exposed in vitro to Listeria and then treated with a lytic peptide. Additionally, resident macrophages from normal non-Listeria immune mice were infected in vitro with Listeria (L2) and treated with the Shiva I peptide. The Shiva peptide had little effect on control resident macrophages (RI). Neither Listeria alone nor the peptide alone (without Listeria infection) resulted in significant cell death. However, Listeria-infected macrophages (L1 and L2) were killed by the peptide. Macrophages from Listeria-immune mice (L1) re-exposed to Listeria by intraperitoneal inoculation 17 hours earlier were killed when exposed to the peptide. The presence of intracellular Listeria was confirmed by microscopic examination of the groups of cells prior to treatment.

As described in greater detail below, we have developed a construct carrying the gene for the native cecropin peptide and the native cecropin promoter, a construct that can be inducibly expressed in animal cells, and that has been successfully expressed in mammalian cells and fish cells. This result is quite unexpected, particularly because a native insect promoter has been successfully used to regulate expression of a gene in mammalian cells. The construct was made so that the native gene, or synthetic genes for analogues of the native peptides, can be placed under the control of the native cecropin promoter.

The plasmid construct designated "PCEP" carries both the native cecropin promoter and the native cecropin gene. Electroporation of the pCEP construct into fetal donkey dermal cells ("FDD cells") resulted in the expression of antibacterial substances when those cells were co-cultured with viable *E. coli.* This antibacterial activity was not observed in control electroporated FDD cells.

Transformation of Fetal Donkey Dermal Cells

Fetal donkey dermal cells were chosen as a model system for cecropin expression. This cell line was chosen for several reasons. First, it was known from prior studies that these cells are resistant to lysis by lytic peptides. Second, this cell line had previously been used to study the antiviral activity of several lytic peptides against Equine Infectious Anemia (EIA) infection. The EIA-infected cells were lysed by the peptides, while uninfected cells were not. The cell line has been demonstrated to be refractory to damage from electroporation. Finally, these cells will act as hosts in vitro for *Listeria monocytogenes* and *Trypanosoma cruzi*, agents to be used to evaluate the antibacterial and anti-protozoal activity of cells expressing native or analog lytic peptides.

FDD cells were cultivated in Eagle's minimum essential medium (MEM), supplemented with Earle's salts, L-glutamine, nonessential amino acids, 5% fetal bovine serum (FBS), and the antibiotics penicillin (100 unit/ml) and streptomycin (100 µg/ml). Cells were split once a week until the desired number were obtained. Conditioned medium that had been clarified from a freshly split culture of FDD cells after 24 hours of culture was used to maintain the cells after electroporation.

Prior to electroporation, FDD cells were rinsed with phosphate buffered saline (PBS), scraped from the flask, rinsed again with PBS, and counted. The concentration of cells was adjusted to $9 \times 10^5$ cells/100 µL, and the cells were placed in a BioRad 0.4 cm (electrode gap width) electroporation cuvette. To this cuvette were also added 400 µL of PBS and 1.4 µg of linearized pCEP DNA. The cuvette and its contents were kept on ice until electroporation. The cells were electroporated at 2.0 KV and 1 µF in the presence of 10 mM IPTG. Immediately after electroporation, 0.5 ml of conditioned medium was added to the cells, which were then incubated on ice for a 10 min recovery period. The cells were then transferred to flasks containing equal parts of conditioned medium and fresh medium, and were allowed to form a monolayer. Monolayered cells were trypsinized, subpassaged in 24-well plates, and allowed to form a monolayer. These cells were then subpassaged into 96-well plates. In the 96-well plates, the cells were grown without any antibiotics, and allowed to form a monolayer.

A two-step method was used to enrich for the population of cells expressing the antibacterial substance. It has been observed that antibacterial activity in cells expressing lytic peptides is associated with a loss of cellular sensitivity to trypsin. This trait allowed the selective removal of cells not expressing the antibacterial substance. Cultures were first exposed to *E. coli*, followed by exposure to trypsin. Cultures demonstrating antibacterial activity were scraped to remove the trypsin-resistant cells. These trypsin-resistant cells were then further diluted and subcultured. Those cells continued to divide to produce a monolayer culture of FDD cells resistant to bacterial colonization. Cultures of cells expressing antibacterial activity were demonstrated to contain the cecropin gene by Southern blotting. Electroporated cell monolayers unable to prevent bacterial colonization were presumed to be negative for expression of the cecropin gene.

Pathogen Challenges

When the monolayer was complete, a first challenge with pathogenic *E. coli* (isolated from a case of equine cystitis) was added at a concentration of 10 bacteria/well. This low concentration was chosen to attempt to stimulate cecropin production, without overwhelming the culture. In the second challenge, bacteria were added at a rate of 1000/well and incubated overnight. After incubation, the wells were examined for colonization of the bacteria in clumps on the surface of the FDD cell monolayer. Bacterial colonization ranged from wells with no bacterial colonies to wells overgrown with bacterial colonies. Wells in which there was no colonization or only slight colonization (about 15% of the total) were rinsed, and antibiotic medium was added back to the wells. Cells were harvested and transferred to flasks to allow monolayer formation. It was observed that the FDD cultures that prevented colonization of bacteria also showed a loss of trypsin sensitivity. This same phenotypic trait had previously been observed in FDD cells following exposure to exogenous cecropin analogs.

The transformed FDD cells expressed the cecropin gene inductively, rather than constitutively. When the cells were split before exposure to bacteria, they were susceptible to treatment with trypsin; but after exposure to bacteria and subsequent cecropin production, the cells were resistant to trypsinization.

FDD cells positive and negative for antibacterial activity were expanded in 75 cm² flasks Both groups of cells were challenged with $10^3$–$10^5$ EIA viral particles and incubated at 37° C. Daily examination of the cells showed the negative control cells acting as normally-infected EIA cells. However, the FDD cells positive for antibacterial activity demonstrated an increased cytopathic effect, manifested approximately 3 days before that of the control cells. This increased cytopathic effect is believed to be due to cecropin production by the FDD cells, a hypothesis that will be tested through a series of deletion mutations, as described below. These results demonstrate the usefulness of the present invention in treating virally-infected cells.

Electroporation of FDD cells has been repeated five times, and bacterial challenges have been performed on all five groups. Cells positive for antibacterial activity have been detected in each of the groups. Cells from the earliest electroporations have been passaged numerous times; they have also been frozen and brought back to culture; all without any apparent loss in viability or phenotypic changes. The incorporation of DNA appeared to be stable: cecropin mRNA was detected in cells descended from the first electroporation that had subsequently been passaged four times.

Confirmation of Transformation by Southern Blot

Southern blot analysis was performed both on FDD cells that were positive for antibacterial activity, and on FDD cells that were negative for antibacterial activity. Electroporated cells not receiving DNA were used as negative controls in the Southern analysis. The chromosomal DNA was harvested from FDD cells using the protocol of Ausubel et al., Current Protocols in Molecular Biology, vols. 1 and 2 (1991) for tissue-culture cells, and that DNA was electrophoresed on a 0.8% agarose gel. The DNA was transferred from the gel to a positively charged nylon membrane (Zeta Probe GT; Bio-Rad Laboratories, Richmond, Calif.), where it was probed with the cecropin gene isolated from pMON 200. The probe was prepared, and the subsequent hybridization was performed, using the non-isotopic Genius 1™ nonradioactive DNA labelling and detection kit (Boehringer Mannheim Corporation, Indianapolis, Ind.). The high stringency protocol was performed according to the manufacturer's instructions. Positive hybridization results were observed only in the electroporated cells receiving pCEP DNA, and in the pCEP vector used as a positive control No hybridization was seen in the electroporated cells that did not receive pCEP DNA.

Confirmation of Transformation by PCR

FDD cells positive for cecropin were rinsed with PBS and fed with MEM that contained antibiotics as described above. The positive clones were passaged three times to try to insure that no cecropin or associated mRNA remained in the cells. After the third passage formed a monolayer, the cells were split into two groups. One group was challenged with bacteria, and the second group received a PBS treatment without bacteria as described above. After a 24-hour incubation, both groups were harvested, and RNA was harvested by the method of Ausubel et al., Current Protocols in Molecular Biology, vols. 1 and 2 (1991). Briefly, 3.5 ml of 4 M guanidinium thiocyanate solution was added per each $10^8$ cells, both to lyse the cells and to inactivate any RNase present. The resulting lysate was suspended in 5.7 M cesium chloride, and centrifuged at 150,000× g for 16 hours to separate RNA from DNA. The RNA pellet was resuspended in TES (10 mM TrisHCl, pH 7.4; 5 mM EDTA; 1% sodium dodecyl sulfate (SDS)), 3 M sodium acetate, and 100% ethanol, and then placed on dry ice/ethanol for 30 min to precipitate the RNA. The pelleted RNA was resuspended in 200 µL of sterile, distilled water, and quantitated by measuring absorbance at 260 nm and 280 nm.

The poly(A)-RNA (i.e., mRNA) was then separated from the tRNA and rRNA as follows. Total RNA was denatured by heating to 70° C. for 10 minutes to expose any poly(A)+ sites, and to disrupt secondary structures. The RNA mixture was passed through an oligo(dT) column to bind the poly (A)+ sites. The column was then washed twice to remove rRNA and tRNA, and then 2 mM EDTA/0.1% SDS was used to elute the mRNA. The mRNA was precipitated with ethanol and sodium acetate, and resuspended in TE (10 mM TrisHCl, pH 8.0, and 1 mM EDTA).

The mRNA was then used for PCR amplification using the semi-quantitative protocol of Dallman et al., "Semi-quantitative PCR for the analysis of gene expression," in Rickwood et at. (eds.), PCR: A Practical Approach (1991). Briefly, synthesis of cDNA from the mRNA was performed with reverse transcriptase from Moloney murine leukemia virus (Gibco-BRL). Using primers to the prececropin gene sequence, the cDNA was then amplified via PCR: cycle at 94° C., 1 min (denaturing); at 55° C., 2 min (annealing); and at 72° C. 1 min (extension). After 10–20 cycles, 15 µL samples can be taken at the end of every 5th cycle, and stored in 96-well microtiter plates. Quantitation of the unknown cDNA was achieved by having internal oligonucleotide standards that were titrated against the cDNA. The concentration of the standard at which the amount of amplification product was equal to the amount of amplification product from the target approximated the starting concentration of the experimental DNA (to within, say, an order of magnitude).

One group of transformed FDD cells was challenged with bacteria for 6 hours, after which the cells were harvested for mRNA isolation. Purified mRNA was reverse-transcribed to cDNA using Moloney Murine virus reverse transcriptase. Following the procedure described above, the CDNA was added to a PCR-amplification mixture with primers to pre-cecropin B, and was cycled 30 times in the thermocycler. FDD cells without vector DNA were used as negative controls. The mRNA from one group of cells showing antibacterial activity had a 180 bp fragment that corresponded to the size that was expected to be amplified, based on the design of the primers This band was not present in the control cell mRNA, nor in the non-challenged cecropin-transformed FDD cells, showing that the cecropin was not constitutively produced.

Acute Phase Response Mechanisms

Our results demonstrate the ability of FDD cells to recognize the native cecropin promoter, and to express the cecropin B peptide in response to exposure to pathogenic *E. coli*. Replication of the cells was not affected. More generally, we expect that a wide variety of animal cells will express genes placed under the control of exogenous promoters responsive to inducers of acute-phase proteins or peptides, due to the high degree of homology many such proteins and peptides have maintained across widely-separated taxa.

Without wishing to be bound by this theory, the fact that the insect promoter was appropriately induced in a mammalian cell suggests that there is substantial homology between the acute phase response (APR) mechanisms of insect cells and mammalian cells—sufficient homology that the mammalian cells recognize the insect promoter and express the gene controlled by that promoter.

Various APR's from various species that have been identified to date share certain similarities at the genetic level, similarities that may be related to their transcription. Known IL-1 sequences, tumor necrosis factor (TNF), human lymphotoxin (LT), human and mouse granulocyte-macrophage colony stimulating factors (GM-CSF), and fibronectin sequences have a common 8 base sequence—TTATTTAT— in the region of the gene that is transcribed into an untranslated portion of the 3' end of the mRNA. Although the function of this sequence is not known, it is believed to influence the termination codon in some fashion; in homologous molecules in different organisms, e.g., human and mouse IL-1, the distance to the termination codon is conserved. Alternatively, it may serve as a possible target for endoribonucleases involved in the rapid removal of mRNA when inflammation ceases. Caput et al., "Identification of a common nucleotide sequence in the 3'-untranslated region of mRNA molecules specifying inflammatory mediators," Proc. Natl. Acad. Sci. USA, vol. 83, pp. 1670–1674 (1986); Toniatti et al., "Regulation of the Human C-reactive Protein Gene, a major marker of Inflammation and Cancer," Mol. Biol. Med., vol. 7, pp. 199–212 (1990). This conserved octamer has recently been identified in the gene for the LPS-binding protein of the American cockroach, *Periplantea americana*. Jomori et al., "Molecular Cloning of cDNA for Lipopolysaccharide binding Protein from the Hemolymph of the American Cockroach, *Periplaneta americana*," J. Biol. Chem. vol. 266, pp. 13318–13323 (1991).

Another common APR sequence in the portion of the gene corresponding to the 3' untranslated region of the mRNA's appears to be the sequence ATTTA, a sequence that is believed to be responsible for unstable mRNA. Jomori et al., "Molecular Cloning of cDNA for Lipopolysaccharide binding Protein from the Hemolymph of the American Cockroach, *Periplaneta americana*," J. Biol. Chem. vol. 266, pp. 13318–13323 (1991). Also identified as conserved regions in many APR's are gene sequences corresponding to non-translated sequences in the 5' end of the mRNA's. One such sequence is TGGRAA, which has been reported for α2-macroglobulin, α1-acid glycoprotein, γ-fibrinogen, haptoglobin and human C-reactive protein (CRP). Dente et al., "Structure of the Human $α_1$-acid glycoprotein gene: sequence homology with other human acute phase protein genes," Nucl. Acids Res., vol. 13, pp. 3941–3952 (1985); Fey et al., "Regulation of rat liver Acute-Phase genes by Interleukin-6 and production of hepatocyte stimulating factors by rat hepatoma cells," Ann. N.Y. Acad. Sci. vol. 557, pp. 317–331 (1989); Toniatti et al., "Regulation of the Human C-reactive Protein Gene, a major marker of Inflammation and Cancer," Mol. Biol. Med. vol. 7, pp. 199–212 (1990). Other conserved 5' transcription factors include the CCAAT/enhancer binding protein (C/EBP) and the CCATT box and enhancer core sequences which are common in a wide range of APR associated gene sequences. Kaling et al., "Liver-Specific Gene Expression: A-Activator-Binding Site, a Promoter Module Present in Vitellogen and Acute-Phase Genes," Mol. Cell. Biol., vol. 11, pp. 93–101 (1991).

Conserved APR sequences for other molecules were compared to Xanthopoulas' published sequence for the native cecropin. Xanthopoulas et al., "The structure of the gene for cecropin B, an antibacterial immune protein from *Hyalophora cecropia*," Eur. J. Biochem., vol. 172, pp. 371–376 (1988) Though not described by Xanthopoulos et al., several sequences were found corresponding to conserved sequences for other APR's. The first conserved sequence found was in the 3' untranslated region—TTATTTAT—found at positions 814–821 and at 972–979, and found again at position 848–855 with only one base substitution. The conserved sequence ATTTA corresponding to unstable mRNA is found in the 3' untranslated region a total of six times. In the 5' untranslated region of the cecropin gene, the sequence TGGRAA is found twice with one base substitution in each sequence, but whether this sequence is functional remains to be determined. A conserved sequence corresponding to the CCATT box and to the enhancer core is found two times in the 5' untranslated region of the gene. With the benefit of hindsight, these homologies make plausible our discovery that the native cecropin B promoter and peptide gene respond to at least some vertebrate APR inducers to elicit expression in vertebrate cells.

It is believed (without wishing to be bound by this theory) that an as-yet-unidentified cytokine is responsible for eliciting both cecropin production and secretion. Unpublished data from our laboratory suggests that cecropin is produced in the moth in response to the presence of a cytokine. Injection of the pupal stage of the giant silkworm moth with either *E. coli* or *E. coli* LPS (lipopolysaccharide or endotoxin), or with human recombinant interleukin-1 resulted in hypertrophic changes in the fat body of the pupae, and in elevated levels of cecropin in the hemolymph. Without wishing to be bound by this theory, it is believed that a cytokine or similar inducing agent is responsible for inducing expression of the gene in vertebrate cells as well when the native moth promoter is used to control the gene.

The Cecropin Promoter

The function of the cecropin promoter will be studied by inserting the neo-CAT gene (chloramphenicol acetyl transferase, a reporter gene) under its control in place of the lytic peptide gene. Transformed cells will be screened by assaying for CAT enzyme activity. The neo-CAT gene was chosen because it will allow pre-selection of FDD cells containing the CAT gene by selecting in the presence of neomycin. Once a transformed cell line with the CAT gene is established, cecropin promoter activity will be studied by altering the promoter with point and/or deletion mutations in the conserved promoter binding sequences, and assaying for altered CAT expression. The neo-CAT gene will be digested from the vector pMAMneo-CAT (Clontech, Palo Alto, Calif.) and inserted into the Sal I site of pCEP to replace the cecropin peptide gene. The conserved 5' APR signals in the cecropin promoter will be altered by oligo-directed mutagenesis as described by Zoler et al., Methods Enzymol., vol. 100, pp. 468–500 (1983). Briefly, ssDNA from construct 5'Δ-94 will be used as a template for the in vitro synthesis of the complementary strand The mutations are designed to insert into a Bal I restriction cite. A set of synthetic oligonucleotides carrying the base substitution(s) are used as primers for the second strand. The mutant cecropin promoter is then cloned into the Bal I site of pCEP linked to the CAT gene. Using this approach, substitutions will be created in the conserved CCATT, TTGGACA, and TTGGAAC sequences of the promoter.

Electroporation will be performed as described earlier, and enzyme production will be screened by SDS-PAGE and Western blot analysis with rabbit anti-CAT. The intact cecropin gene (including the unaltered promoter) will be run simultaneously in all assays for comparison. Identification of the antibacterial substance as cecropin B, and its localization within FDD cells and on their surface, will be accomplished using rabbit anti-cecropin B polyclonal antibodies with an indirect fluorescent antibody procedure.

The intact cecropin B gene and the neo-CAT gene in pCEP will be run concurrently in the following experiments to probe the means of expression. Cecropin- and neo-CAT-producing FDD cells will be prepared as described above using the bacterial, LPS, or IL-1 challenge method. Cells positive for cecropin and neo-CAT will be rinsed with PBS and cultured in MEM containing antibiotics. The positive clones will be passaged three times to insure that no cecropin, CAT enzyme, or RNA's associated with their production are left in the cells. After each third passage forms a monolayer, the cells will be split into two groups; one group will be challenged with bacteria in PBS, and the second group will receive a PBS treatment without bacteria. After a 24-hour incubation, the RNA from both groups will be harvested as described by the method of Ausubel et al., Current Protocols in Molecular Biology, vols. 1 and 2 (1991), as described above.

The mRNA is then used for PCR amplification using the semi-quantitative protocol previously described, using primers to the pre-cecropin and CAT gene sequences. If, as expected, cecropin and CAT expression is induced, then only cells exposed to the bacteria or cytokine will yield positive results for the mRNA. If, however, either protein is constitutively produced, then both the negative controls and the "induced" cells will demonstrate a positive response for mRNA; and if this is the case the quantitative portion of this experiment will determine whether the levels increase in response to the inducing agent.

To understand how the cell is induced to produce cecropin, responses to various agents will be measured. The same experiments will be conducted on cells containing vectors in which the cecropin promoter has been altered. In the unlikely event that the cecropin promoter is determined not to be the promoter responsible for cecropin production, then the primers made to the cecropin and/or CAT genes will be used to sequence into the FDD genome to identify and characterize the active promoter. Purified LPS (Sigma Chemical) will be added to cells negative for cecropin production; the supernatant will be collected; and the LPS will be removed with neutralizing antibody (anti-LPS). Four groups of cells will then be exposed to different inducing agents: (1) LPS-induced-cell supernatant treated with anti-LPS and polymyxin B to remove LPS; (2) IL-1 added to the FDD cells; (3) FDD cells induced with whole bacteria; and (4) FDD cells receiving a PBS placebo as a control. The supernatant will be collected from each group and split into two groups: half of the supernatant will be used to determine cecropin activity on *E. coli* or CAT activity, and the other half will be quantitated for the amount of cecropin or CAT production using a polyclonal anti-cecropin or anti-CAT. Some of the supernatant from the LPS-induced group and the IL-1-induced group will be treated with anti-IL-1 and used to challenge cecropin-producing cells. Cecropin or CAT production will be measured using the bacterial assay and the polyclonal antibody to cecropin or CAT.

If LPS alone is responsible for inducing cecropin expression, then only the LPS and bacteria-induced FDD cells should show a positive cecropin or CAT response. If IL-1 is responsible for induction, then all of the cells except the control should show a positive response, and this response should be neutralized with anti-IL-1, which would then yield a negative result for cecropin or CAT when the supernatant is used to induce FDD cells. Other cytokines (e.g., IL-6, TNF (Biogen), IL-2 (Bioferon), and purified γ-IFN (Bioferon)) will be assayed in a similar fashion.

Other Promoters

Promoters other than the native cecropin promoter are suitable for use in the present invention. Such promoters include other native promoters for native lytic peptides, and other native promoters that are responsive to APR inducers. The identification and isolation of such promoters is within the ability of one of ordinary skill in the art, given the teachings of the present specification, including particularly the following discussion.

Where such promoters are not already identified in the literature, they may be identified as follows. With a lytic peptide, the DNA upstream from the coding region of the gene may be sequenced, and the portion comprising the promoter identified through standard means, by searching for conserved sequences that are typical of promoters.

APR inducers, such as IL-1, IL-2, IL-6, C-reactive protein, LPS binding protein, lymphotoxin, granulocyte-macrophage colony stimulating factors, fibronectin, interferons, and tumor necrosis factor, induce other genes as well. Genes induced by an APR inducer may be identified through means known in the art, including isolation of the proteins thus translated, or identification of induced mRNA's through subtractive hybridization. Where the protein is isolated, through means known in the art: it may be partially sequenced; a probe for a genomic library or (preferably) for an appropriate cDNA library may be prepared; and the cloned gene may then be sequenced, including its promoter region.

Construction of Plasmid pCEP, and Transfection of *E. coli* with pCEP

The plasmid pCEP is a pBR322 derivative that carries the gene for ampicillin resistance and the ColE1 origin of replication, but in which a segment from base pair 105 to base pair 2345 has been deleted to streamline the plasmid, to allow incorporation of the native cecropin promoter and gene, or other gene of interest. The cecropin gene segment is the 5.9 Kb fragment isolated from the vector pMON 200 by a restriction digest with EcoR I and Xho I. Both ends were filled to create a blunt-ended fragment, as were the ends of the pBR322 plasmid.

The native cecropin gene was ligated into the modified pBR322 vector to give a construct of 9.3 Kb, using a modification of Ausubel et al., Current Protocols in Molecular Biology, vols. 1 and 2 (1991); and Sambrook et al., *Molecular Cloning, A Laboratory Manual*, $2^{nd}$ ed. (1989). The modification, discussed further below, increases the chance of blunt-end fragment insertion into the plasmid. The resulting recombinant plasmid, designated pCEP, was then electroporated into *Escherichia coli* NM554 (Stratagene, La Jolla, Calif.) using a BioRad Gene Pulser™ electroporator, under conditions described by the manufacturer for *E. coli*. Electroporated bacteria were plated onto Brain-Heart Infusion (BHI) agar containing 50 μL/ml of ampicillin, and incubated at 37° C. overnight. Because the ptac promoter is not read unless induced, the potentially lethal lytic peptide gene may be maintained in *E. coli* without the danger that the peptide will kill the *E. coli*.

It is preferred that the promoter controlling the transcription of the transposase be inducible, so that the transposase gene is not transcribed until an inducing stimulus (e.g., IPTG for the ptac promoter) is supplied. However, it would also be possible to use a constitutive promoter for the transposase, particularly a promoter that is inactive in *E. coli* or other prokaryotic host, but that is expressed constitutively in a eukaryotic cell. The vector would be lost or diluted following a number of cell divisions, so that continuing transpositions of the inserted segment should not occur.

Colonies growing on the BHI/ampicillin plates were subcultured in BHI/ampicillin broth for plasmid screening (Qiagen, Chatsworth, Calif.) and freezing at −70° C. Plasmid preparations of the isolates were examined by agarose gel electrophoresis. A 1% gel was electrophoresed for 4 hours at 4 V/cm, stained with 0.4 μg/ml ethidium bromide for 10 min., and destained in distilled water for 30 min. A supercoiled plasmid DNA ladder (Sigma Chemical) was used as a DNA size reference; bands corresponding to ~9.3 Kb were removed from the agarose and purified using the Eluquick™ DNA Purification Kit protocol. Purified plasmid DNA was then electroporated back into competent *E. coli* NM554 and selected on BHI/ampicillin plates. Because *E. coli* NM554 is a plasmid-less strain, this additional purification-electroporation step insured that there was only one plasmid type per cell by eliminating pBR322—pBR322 self-ligated dimers.

Confirmation of the pCEP plasmid was obtained by growing *E. coli* NM554 on BHI/ampicillin plates; making plasmid preparations; making restriction digests with BamH I to yield two fragments of 2.3 and 7.0 Kb; and Southern blotting of the restriction digest under very stringent conditions using the cecropin gene isolated from pMON 200 as a probe.

A sample of this transformed *E. coli* strain NM554 containing plasmid pCEP with the cecropin gene was deposited with the American Type Culture Collection (ATCC), 12301 Parklawn Drive, Rockville, Md. 20852 on Jun. 30, 1993, and was assigned ATCC Accession No. 69342. This deposit was made pursuant to a contract between ATCC and the assignee of this patent application, Board of Supervisors of Louisiana State University and Agricultural and Mechanical College. The contract with ATCC provides for the permanent and unrestricted availability of the progeny of this *E. coli* strain to the public on the issuance of the U.S. patent describing and identifying the deposit or the publication or the laying open to the public of any U.S. or foreign patent application, whichever comes first, and for availability of the progeny of this *E. coli* strain to one determined by the U.S. Commissioner of Patents and Trademarks to be entitled thereto under pertinent statutes and regulations. The assignee of the present application has agreed that if the *E. coli* strain on deposit should die or be lost or destroyed when cultivated under suitable conditions, it will be promptly replaced on notification with a viable culture of the same *E. coli* strain. As the term is used in the claims below, it should be understood that the "pCEP" plasmid encompasses not only the specific plasmid included in this ATCC deposit, but also any plasmid that is substantially identical to that plasmid, with the specific exception that the gene placed under the control of the cecropin promoter may vary; it is intended that the term "pCEP" plasmid should encompass any such plasmid, regardless of the specific DNA inserted.

After confirmation of the pCEP plasmid was completed, a large scale plasmid isolation was performed. A 250 ml culture of the transformed *E. coli* was grown in BHI/ampicillin broth on a rotary shaker at 37° C. until an absorbance at 600 nm of $A_{600}$=0.4 was obtained, at which time chloramphenicol was added to give a final concentration of 180 µg/ml before amplifying the plasmid. Shaking was continued overnight. After 24 hours, the pCEP DNA was harvested using the Qiagen plasmid isolation protocol (Qiagen, Chatsworth, Calif.) and column to obtain pure, high quantity (0.7 µg/µL) plasmid DNA. A restriction digest using Pst I was conducted on 20 µg of the pCEP DNA to linearize the DNA prior to electroporation into a mammalian cell line as described above. The enzyme Pst I was chosen because it linearizes the plasmid without cutting the cecropin gene.

The pCEP plasmid itself was constructed as follows. Plasmid pNK2859 containing Tn10 derivative 103 (obtained from Dr. Nancy Kleckner, Department of Biochemistry and Molecular Biology, Harvard University; see Kleckner et al., "Uses of Transposons with Emphasis on Tn10," pp. 139–180 in Miller (ed.), *Methods in Enzymology*, vol. 204 (1991)) was digested with the enzyme BamH I. This digestion had the effect of removing the kanamycin antibiotic resistance marker from the transposon, but leaving the insertion sequences flanking the kanamycin resistance gene intact. The digest resulted in two bands approximately 3.2 Kb and 1.6 Kb in size. A double digestion was performed on the pMON 200 vector with the enzymes EcoR I and Xho I, yielding fragments of approximately 6 Kb and 9.7 Kb. These two enzymes remove the native cecropin B gene intact from the pMON 200 vector in the 6 Kb fragment. The resulting fragments from the two digests were separated by agarose gel electrophoresis on a 1% gel run at 40 V for four hours. The 3.2 Kb fragment from the transposon vector, and the 6 Kb fragment from the pMON 200 vector were excised from the gels, and each was separated from the agarose using the Eluquick™ DNA Purification Kit (Schleicher and Schuell, Keene, N.H.). This method minimized DNA shearing, and allowed efficient recovery of the desired fragments.

The purified DNA fragments did not have complimentary ends, so a blunt-end ligation protocol was designed, based on modifications of Ausubel et al., Current Protocols in Molecular Biology, vols. 1 and 2 (1991); and Sambrook et al., *Molecular Cloning, A Laboratory Manual*, $2^{nd}$ ed. (1989). Briefly, blunt end fragments were created using Klenow fragment and dNTP's (final concentration of 0.5 mM) at an incubation temperature of 30° C. for 15 min, followed by deactivation at 75° C. for 10 min. Both the cecropin fragment and the transposon vector fragment were extracted in phenol:chloroform; precipitated in isopropanol; and resuspended in 10 µL of TE buffer (10 mM Tris, 5 mM EDTA, pH 8.0). The cecropin fragment was then ligated onto the transposon vector fragment using T4 DNA ligase and 40% PEG (polyethylene glycol) according to Sambrook et al., *Molecular Cloning, A Laboratory Manual*, $2^{nd}$ ed. (1989). PEG was used to enhance the ligation of blunt-ended fragments, and to minimize the formation of concatemers of the same DNA.

The ligation mixture was incubated overnight at 20° C. The following day DNA was extracted in phenol:chloroform; precipitated in isopropanol; and resuspended in 10 µL of sterile, distilled $H_2O$. *E. coli* NM554 (Stratagene, La Jolla, Calif.) was made competent for electroporation using the protocol of BioRad, Inc (BioRad Laboratories, Hercules, Calif.). Electroporation was conducted at 1.65 KV, 200 Ω, and 25 µF using $10^{10}$ cells of competent *E. coli*. Two electroporations were performed: (1) $10^{10}$ cells with 5 µL of the ligated cecropin/vector DNA, and (2) a negative control using $10^{10}$ cells with 5 µL of sterile, distilled $H_2O$. Each electroporation mixture was immediately placed in 1 ml of BHI (Brain Heart Infusion, Difco Inc.) broth at 37° C. for one hour to recover, and to begin expression of the ampicillin resistance marker. After the one-hour recovery period, 200 µL of each mixture was applied to an agar plate using the spread plate technique to cover the entire plate. *E. coli* receiving the ligated pCEP plasmid were plated onto BHI agar plates supplemented with 100 µg/ml of ampicillin, while the *E. coli* receiving the distilled $H_2O$ were plated both on BHI agar plates with ampicillin, and on BHI agar plates without ampicillin as controls. All plates were incubated overnight at 37° C. All colonies growing on the BHI/ampicillin agar plates were then grown in BHI/ampicillin broth, and frozen at −70° C.

Each colony was also screened for the presence of a plasmid of approximately 9.391 Kb: 5.99 Kb from the cecropin gene segment, plus 3.401 Kb from the vector DNA. When suitable candidates were identified, the potential pCEP-bearing *E. coli* were propagated in a 100 ml culture of BHI/ampicillin broth grown to an absorbance of $A_{600}$=0.4, at which time chloramphenicol was added to a final concentration of 170 µg/ml. The cultures were allowed to continue shaking overnight at 37° C. for plasmid replication. The pCEP DNA was then harvested using a modified version of the Qiagen (Qiagen, Chatsworth, Calif.) protocol. Insertion of the cecropin B gene was confirmed using Southern blot analysis, with labelled cecropin gene as a probe. The nonisotopic Genius 1™ nonradioactive DNA labelling and detection Kit (Boehringer Mannheim) was used to perform the Southern analysis, and each step was conducted under stringent hybridization conditions. Isolates positive for the cecropin insert were then tested for the production of cecropin B as described above.

Other constructs will also be made. The first of these constructs is a streamlined native cecropin promoter-cecropin B peptide vector. The gene sequence obtained from the pMON 200 vector is rather cumbersome to work with, in that it is 6 Kb long. Using the published sequence and restriction map of cecropin B (Xanthopoulas et al., "The structure of the gene for cecropin B, an antibacterial immune protein from *Hyalophora cecropia*," Eur. J. Biochem., vol. 172, pp. 371–376 (1988)) a construct will be made that includes the entire gene, and that is about 3.1 Kb, about half the size of the 6 Kb sequence. DNA from the pMON 200 vector will be partially digested with EcoR I and BamH I. The fragments will be separated on an agarose gel, and purified with the Eluquick™ DNA Purification Kit protocol described above. These fragments will then be cloned into a pBR322derived plasmid with polylinkers with either EcoR I- or BamH I-complementary ends to the digested fragment to insure proper orientation in the construct.

Streamlining the cecropin insert will allow easier removal of the gene encoding the native peptide, to facilitate replacement with a gene encoding a synthetic peptide such as Shiva I. If needed, another promoter can be substituted for the native cecropin promoter through means known in the art. At this time, however, the native cecropin promoter is preferred.

Creating a smaller delivery vehicle for the cecropin gene will also aid in sequencing the gene in a host cell using nucleic acid amplification techniques such as the polymerase chain reaction ("PCR") Primers can be synthesized that will amplify internal segments of the cecropin gene, or segments extending into the host genome, to determine both the orientation and location of the gene in the host chromosome. A smaller fragment will enable sequencing with less time and expense.

ANOTHER EXAMPLE

Disease-Resistant Catfish

Catfish farming has rapidly become a major agricultural industry in the southeastern United States, particularly in Alabama, Louisiana, Mississippi, Arkansas, and South Carolina. A major factor limiting the economic success and future growth of the catfish industry is disease. Bacterial disease is the primary cause of mortality in commercially-reared channel catfish (*Ictalurus punctatus*), accounting for 57.5% of 9575 total cases examined from 1987 to 1989 by diagnostic labs in Alabama, Mississippi, and Louisiana. Infectious diseases cause an estimated 10% annual mortality in an industry where each 1% loss to disease translates to about a 5.5% loss of profits. The catfish industry could be greatly enhanced if this 55% loss of profits could be reduced.

Vaccination is one possible mechanism for reducing disease caused by bacterial or other pathogens. Of the major bacterial diseases associated with commercially-raised channel catfish, *Edwardsiella ictaluri* is the leading cause of mortality, followed by *Cytophaga columnaris* and *Aeromonas* sp. *E. ictaluri* alone accounts for approximately 50% of the catfish disease cases submitted to aquatic animal diagnostic laboratories in the southeastern United States. Some progress has been made in live attenuated vaccine construction for *E. ictaluri* and *A. hydrophila*. Though a marketable vaccine may be available in the near future for *E.ictaluri,* a vaccine for *A. hydrophila* is many years away, and a live attenuated vaccine for *C. columnaris* may never be feasible due to the difficulty in obtaining viable, stable mutants capable of eliciting an immune response. There remains an unfilled need for improved, inexpensive methods of combatting bacterial and other disease in catfish.

An alternative to creating a vaccine for each pathogen plaguing the catfish industry is to create a transgenic strain of catfish having lymphocytes capable of destroying invading organisms before the disease process is established. Toward this end, we have transformed catfish eggs with the cecropin B gene, using the novel transposon-based pCEP vector.

Plasmid pCEP was replicated in large quantities by amplification in *E. coli* strain NM554. (The same plasmid in the same *E. coli* strain as was deposited with the American Type Culture Collection under accession number ATCC 69342.) Plasmid DNA from the amplified *E. coli* cultures was harvested with Qiagen Maxi-Columns (Qiagen Inc., Chatsworth, Calif.) using the manufacturer's recommended protocol. This procedure typically yielded 500–800 µg/ml of plasmid DNA from 250 ml broth culture. Purified pCEP DNA was linearized by Pst I restriction endonuclease digestion for 2 hours at 37° C. The reaction was stopped by the addition of 3 µl of 0.5 M EDTA, and holding at 70° C. for 10 min. The DNA was purified by phenol:chloroform extraction and isopropanol precipitation. Linearized DNA was resuspended to a concentration of 100 µg/ml in Hanks' balanced salt solution (HBSS), and was stored at 4° C. until it was used in electroporation.

Two healthy, mature, male channel catfish from a research stock maintained at Louisiana State University, Baton Rouge, La. were killed, and their testes were removed as a source for spermatozoa. Adherent tissue was dissected away, and the testes were blotted, dried, and weighed. Two grams of anterior testis from each fish were placed in a plastic bag, and were dissociated by crushing. The spermatozoa were suspended in 10 ml of HBSS, and were stored at 4° C. until used.

Five pairs of healthy, mature (2–4 kg, 50–80 cm long) channel catfish from a research stock maintained at Louisiana State University, Baton Rouge, La. were spawned using standard procedures. Female channel catfish were injected with a luteinizing hormone-releasing hormone analog, D-Ala$^6$ Des Gly$^{10}$ LH-RH-ethyl amide (Peninsula Laboratories, Belmont, Calif.), at a dose of 100 µg/kg, and were paired with male channel catfish in 80 liter aquaria supplied with aerated, flow-through well water. The fish were monitored for spawning behavior. Once egg release had begun, the females were removed from the aquaria, anesthetized in 0.02% tricaine methanesulfonate, rinsed, and dried. Eggs were stripped by application of pressure along the abdomen.

Before fertilization, eggs were electroporated with the linearized pCEP DNA using a BioRad Gene Pulser™ electroporator (Richmond, Calif.). Eggs were rinsed in Hank's buffer and placed in a specially designed cuvette with 3 ml of DNA solution. Approximately 500 channel catfish eggs per treatment were placed in a silicon-coated electroporation chamber (6 cm×6 cm×6 cm). Eggs were either sham-electroporated (control), or were electroporated with 100 µg/ml of linearized pCEP plasmid DNA containing the cecropin gene. The field strength for the electroporation was 125 V/cm, with 200 Ω resistance, and 1 µF capacitance, with each treatment receiving either 1 or 3 pulses with a time constant of 7–10 msec, at a pulse interval of 1 sec.

The DNA solution was then removed, the eggs were rinsed in HBSS, and the electroporated eggs were then fertilized with the previously harvested spermatozoa using standard techniques. The eggs were allowed to water-harden for approximately 15 minutes. Once water-hardened, zygotes were treated with a pH-buffered 1.5% sodium sulfite solution to remove the gelatinous mass, and to inhibit possible fungal colonization. The sodium sulfite solution was then decanted from the zygotes, followed by a water rinse to remove excess sodium sulfite. Zygotes were then placed in hatching jars in a recirculating raceway with aeration, where they were maintained until hatching.

Five days after hatching, fish fry produced from different females and treatments were pooled into two groups: fish that had been electroporated with pCEP DNA, and fish that had been electroporated without exogenous DNA. Thirty-nine potentially transgenic fish, and forty-three sham-electroporated controls were acclimated for two weeks at 27° C. in 95-liter aquaria equipped with both under-gravel and outside filtration.

Six-week-old fry were then challenged with a high dose, 8×10$^5$ cfu/ml (final concentration), of a known virulent strain of *E. ictaluri* by adding the culture to the water. The fry were allowed to swim in the inoculum for 2 hours with aeration, but no filtration. No subsequent water exchanges were conducted, although normal filtration resumed after two hours. Fish were observed three times daily for signs of the enteric septicemia typically caused by *E. ictaluri*. The posterior kidneys of dead or moribund fish were dissociated and used to establish cultures on 5% sheep blood agar plates The plates were incubated at 30° C., and the resulting colonies were screened by biochemical analysis and agarose gel electrophoresis to confirm the presence of *E. ictaluri* in the dead and moribund fish.

Transformed channel catfish were grown to approximately 15 cm in length, and blood samples were collected for assay by the polymerase chain reaction (PCR). Samples of genomic DNA were extracted both from the potentially transgenic channel catfish, and from the blood of control sham-electroporated catfish by the guanidine hydrochloride method. Normal channel catfish DNA was also spiked with cecropin DNA as a positive control. To demonstrate that the PCR procedures were working in samples that were negative for the cecropin gene, as an additional positive control we used primers targeted to the $C_H^4$ exon from the channel catfish gene encoding the constant region of the immunoglobulin $\mu$ heavy chain. The PCR reactions were set up as follows: 10 $\mu$M dNTP's, 1x Taq buffer, 5 units of Taq polymerase, 1% DMSO, 2 mM MgSO$_4$, 0.26 $\mu$M of each PCR primer, and sterile distilled water to 100 $\mu$l. Two primers, AGACTTGACTCCGCTGCATAAGTG (SEQ ID NO. 1) and TACCGTTTCTGATGTTGCGACC (SEQ ID NO. 2), were designed to amplify an 846 bp segment from the genomic cecropin DNA. (These two primers do not anneal to cecropin cDNA.) The reaction conditions were 95° C. for 2 min to denature the template, followed by 35 cycles programmed as follows: 95° C. for 30 sec, 52° C. for 30 sec, and 72° C. for 60 sec. After PCR, the samples were electrophoresed for 2 hours at 6.0 V/cm in a 2% agarose gel containing 0.3 $\mu$g/ml ethidium bromide. Size marker ΦX174, digested with HaeIII (Sigma Chemical Co., St. Louis, Mo.), was used to generate DNA size references. The banding patterns were observed on a MacroVue ultraviolet transilluminator (Pharmacia LKB Biotechnology, Piscataway, N.J.), and were photographed (Photoman PHH Series, Hoefer Scientific Instruments, San Francisco, Calif.).

To determine whether the cecropin gene was transcribed, mRNA was isolated and reverse-transcribed to cDNA for PCR analysis. To test the inducibility of the cecropin gene in response to an invading pathogen, blood samples were taken prior to challenge from channel catfish known to be positive for the cecropin gene and from channel catfish that were siblings, but that had not received the transgene. Then to induce cecropin production, all catfish (transgenic and controls) were challenged by intramuscular injection with 8×10$^8$ irradiated E. ictaluri. Blood samples for mRNA isolation were taken 14 hours after the challenge. Blood was collected from the caudal vessel with a 3-ml syringe and a 22 gauge needle containing 150 $\mu$l ACD solution (Becton-Dickinson, vacutainer #6406) per ml of blood as an anticoagulant. After samples were collected, they were immediately placed in 1-ml cryovials and placed in liquid nitrogen until mRNA isolation.

The mRNA was isolated using the Oligotex™ RNA Isolation reagents and columns (Qiagen, Inc., Chatsworth, Calif.), and reverse-transcribed to cDNA using standard methods. The polymerase chain reaction for the cDNA samples was conducted as described above, except as otherwise described in this paragraph. For the template DNA, a 5 $\mu$l aliquot of the cDNA was used. The primer sequences TTTTCTTCGTGTTCGCTTTGGTTCTG (SEQ ID NO. 3) and ATCGCCGGTCCAGCCTTGACAATAC (SEQ ID NO. 4) were designed to amplify a 135-bp fragment of the cecropin cDNA. These two primers will also amplify a 649-bp fragment of genomic cecropin DNA. As a control, PCR on the plasmid vector was also run, yielding a 649-bp fragment. The annealing temperature was 54° C. for 30 sec. The PCR products were electrophoresed on a 3% agarose gel for 2 hours at 6.0 V/cm, along with the ΦX174/Hae III reference size markers. Samples were optimized with the Invitrogen™ PCR Optimizer kit, using the manufacturer's protocol with 1 unit of Taq polymerase.

The control channel catfish challenged with E. ictaluri demonstrated symptoms of septicemia beginning 10 days after immersion challenge, and began dying on day 11. By day 14, twenty-six of forty-three control fish were dead (60.4% mortality). The potentially transgenic fish did not show signs of septicemia or mortality until day 30. By day 33, thirteen of thirty-nine (33% mortality) of the potentially transgenic fish were dead. Compared to the control, mortality in the experimental group was substantially lower, and occurred substantially later. The mortality among the experimental group is attributed to toxic shock from the abnormally high concentrations of E. ictaluri used in this experiment. Future experiments are planned at lower concentrations of pathogen to test this hypothesis. The survivors from this experiment were used in the PCR experiments to detect presence or absence of the cecropin gene.

With the genomic-targeted primers (SEQ ID NOS. 1 and 2), PCR was expected to amplify an 846-bp fragment from the genomic cecropin gene. The values calculated by linear regression for both the positive control and the positive bands for the channel catfish on the agarose gel were 820 bp, within limits of experimental error. Of 18 potentially transgenic catfish assayed for the presence of the cecropin B gene, 9 (or 50%) yielded positive bands for that gene, while none of the 10 negative control fish assayed to date had such a band. All samples, both control and experimental, were positive for the heavy chain immunoglobulin exon, demonstrating that the PCR procedure worked properly.

The primers targeted to cecropin cDNA will yield a 135 bp fragment following PCR amplification. The same primers will amplify a 649 bp fragment when used to assay genomic DNA, the difference lying in the excision of an intron. These expected 649 bp and 135 bp bands were in fact observed following PCR amplification of genomic DNA and cDNA, respectively, from the challenged experimental fish. These bands were absent from all the controls, including the pre-challenge mRNA/cDNA from the blood of the same fish that later tested positive for cecropin mRNA/cDNA after E. ictaluri challenge, demonstrating that transcription of the cecropin mRNA was induced by the pathogen challenge.

The data clearly demonstrated that the cecropin B gene was stably inserted into the genome of channel catfish with the pCEP vector at high efficiency, and that the gene is inductively expressed in response to an important catfish pathogen, Edwardsiella ictaluri. Experiments to detect cecropin B mRNA from blood drawn from the same catfish will be performed using standard techniques known in the art (see, e.g., the procedures described above to detect mRNA from FDD cells). These experiments are expected to demonstrate the expression of the cecropin B gene in the transformed catfish.

FURTHER EXAMPLES

Making Transgenic Bony Fish via Lipofection, with Channel Catfish and Koi as Exemplary Embodiments A drawback to working with many species of fish, including channel catfish, is the length of time required for the fish to reach sexual maturity—typically 3–4 years for channel catfish. When transgenic catfish are generated by electroporating eggs as described above, a minimum of three years must therefore elapse before the heritability of the transgene can be established with certainty. While we have every reason to believe that the transgene will be transmitted to offspring, heritability cannot be established with certainty until actual offspring can be examined.

Lipofection provides an alternative method of creating transgenic broodstock (probably mosaics), at least a portion of whose gametes will contain the transgene. If lipofection is performed before the gonads recrudesce in spring (i.e., preferably in late winter), then natural spawning can take place, and the heritability of the transgene can be evaluated more quickly. In many applications, production of transgenic fish by lipofection may also be more economical than electroporation.

Lipofection uses a cationic lipid to deliver DNA to cells. The liposome is a unilamellar lipid membrane with both polar and nonpolar faces. When liposomes are mixed with DNA in aqueous solution, essentially all the DNA is encapsulated by the polar side of the lipid membranes, leaving the nonpolar surface exposed to the exterior. The nonpolar surface later interacts and fuses with nonpolar cell membranes to deliver DNA into cells, whether the cells be in cell culture, or in vivo.

As an initial demonstration of the lipofection technique, sexually immature catfish were used, because smaller fish are easier to handle than larger fish. Twenty specific pathogen free channel catfish (catfish that had never been exposed to *E. ictaluri*) were obtained from the Aquatic Pathobiology Laboratory at the School of Veterinary Medicine, Louisiana State University, Baton Rouge, La. Five fish per treatment were acclimated at 26° C. for two weeks in 35 liter aquaria equipped with both under-gravel and outside filtration. Once acclimated, these fish were used for lipofection.

Lipofectin™ reagent (Gibco BRL, Gaithersburg, Md.) was used per the manufacturer's instructions to encapsulate the linearized pCEP DNA. Briefly, 15 μL of Lipofectin™ reagent and 2.0 μg of linearized pCEP DNA were mixed together, and then incubated for 15 min. Following incubation, the following intraperitoneal injections were made into the channel catfish:

Group 1, 15 μL Lipofectin™/2.0 μg pCEP complex in 100 μL 0.85% NaCl solution +0.5 mL IPTG Group 2, 2.0 μg pCEP in 100 μL 0.85% NaCl solution +0.5 mL IPTG Group 3, 2.0 μg pCEP in 100 μL 0.85% NaCl solution Group 4, 15 μL Lipofectin™ in 100 μL 0.85% NaCl solution Intraperitoneal injections were made because the gonads and hematopoietic organs are exposed to the cavity, giving the liposome/DNA complex direct access to the organs for fusion to occur.

The fish were held for ten days, and then 0.1 mL blood in sodium citrate was withdrawn per fish from the caudal vein. DNA was extracted from the blood using the QiaAmp™ Blood Kit (Qiagen Inc., Chatsworth Calif.). PCR was conducted on each sample as described previously, using as primers SEQ ID NOS. 1 and 2, and the reaction products were electrophoresed on a 2% agarose gel. The pCEP vector DNA was used as a positive control in the PCR reactions.

All 5 Group 1 fish tested positive for the cecropin B gene, while none of the fish from Groups 2, 3, and 4 tested positive. It is expected that the cecropin B gene was incorporated into the gonads, and will be expressed in offspring Similar experiments will also be performed on sexually mature channel catfish, so that offspring may be tested more quickly.

We have also performed a pCEP lipofection on two sexually mature male Koi, following the lipofection procedure described above. Testing is currently underway to confirm that the cecropin B gene can be detected in sperm from these lipofected Koi, and that the cecropin B gene will be appropriately expressed inductively in the offspring of these Koi.

Miscellaneous

The complete disclosures of all references cited in this specification are hereby incorporated by reference, as are the complete disclosures of the three priority applications International Application No. PCT/US94/07456, international filing date Jun. 30, 1994; U.S. patent application Ser. No. 08/085,746, filed Jun. 30, 1993 abandoned; and U.S. patent application Ser. No. 08/084,879, filed Jun. 30, 1993 abandoned.

We claim:

1. A transgenic catfish whose genome comprises a gene encoding cecropin B operably linked to the native cecropin B promoter, wherein said cecropin B promoter functions to direct expression of the cecropin B gene; and wherein the expression of said cecropin B gene imparts resistance to pathogenic bacteria.

2. A transgenic koi whose genome comprises a gene encoding cecropin B operably linked to the native cecropin B promoter, wherein said cecropin B promoter functions to direct expression of the cecropin B gene; and wherein the expression of said cecropin B gene imparts resistance to pathogenic bacteria.

3. A transgenic bony fish whose genome comprises a gene encoding cecropin B operably linked to the native cecropin B promoter, wherein said cecropin B promoter functions to direct expression of the cecropin B gene; and wherein the expression of said cecropin B gene imparts resistance to pathogenic bacteria.

* * * * *